| United States Patent [19] | [11] | 4,101,580 |
|---|---|---|
| Inamoto et al. | [45] | Jul. 18, 1978 |

[54] 3-AMINO-4-HOMOISOTWISTANE AND AN ACID ADDITION SALT THEREOF AND A PROCESS FOR PRODUCING THE SAME

[75] Inventors: Yoshiaki Inamoto; Hiroshi Ikeda; Yoshiaki Fujikura, all of Wakayama; Naotake Takaishi, Iwade, all of Japan

[73] Assignee: Kao Soap Co., Ltd., Tokyo, Japan

[21] Appl. No.: 695,983

[22] Filed: Jun. 14, 1976

[30] Foreign Application Priority Data

Jun. 27, 1975 [JP] Japan ................................. 50-79437

[51] Int. Cl.$^2$ ............................................. C07C 87/32
[52] U.S. Cl. .................................. 260/563 P; 424/325
[58] Field of Search ..................................... 260/563 P

[56] References Cited

U.S. PATENT DOCUMENTS

| 3,397,233 | 8/1968 | Cairns | 260/563 P |
| 3,449,422 | 6/1969 | Miller | 260/563 P |
| 3,470,248 | 9/1969 | Brotherton et al. | 260/563 P |
| 3,729,513 | 4/1973 | Berezin | 260/563 P X |

OTHER PUBLICATIONS

Aigami et al., "J. Med. Chem.", 19, 536 (1976).

*Primary Examiner*—Paul F. Shaver
*Attorney, Agent, or Firm*—Oblon, Fisher, Spivak, McClelland & Maier

[57] ABSTRACT

This invention relates to novel 3-amino-4-homoisotwistane (3-amino-tricyclo [5.3.1.0$^{3,8}$] undecane), an acid addition salt thereof, and to a process for producing the same.

4 Claims, No Drawings

3-AMINO-4-HOMOISOTWISTANE AND AN ACID ADDITION SALT THEREOF AND A PROCESS FOR PRODUCING THE SAME

BACKGROUND OF THE INVENTION

Description of the Prior Art

Heretofore, it has generally been known that adamantylamine hydrochloride, one of the adamantane derivatives which falls within the class of cage-molecular hydrocarbons, displays antiviral activity and is effective in the treatment of Parkinson's disease.

SUMMARY OF THE INVENTION

The present inventors have examined a wide variety of 4-homoisotwistane (tricyclo [5.3.1.0$^{3,8}$] undecane) derivatives, which are cage-molecular hydrocarbons of the same type as adamantylamine hydrochloride, and have found that a new compound 3-amino-4-homoisotwistane represented by the following formula [I], and acid addition salts thereof exhibit superior antiviral effects:

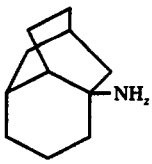
[I]

The present compound, 3-amino-4-homoisotwistane, in which an amino group is directly bound to the carbon framework of 4-homoisotwistane, has never been synthesized before.

It is, therefore, one object of this invention to provide novel 3-amino-4-homoisotwistane which possesses a superior antiviral activity.

Another object of this invention is to provide a novel process for producing 3-amino-4-homoisotwistane.

According to the present invention, 3-amino-4-homoisotwistane of the formula [I] is produced by reacting 3-substituted-4-homoisotwistane of the formula [II] with acetonitrile in the presence of sulfuric acid, thereby forming 3-acetylamino-4-homoisotwistane of the formula [III] and hydrolyzing the resulting compound, as is shown by the following reaction formula:

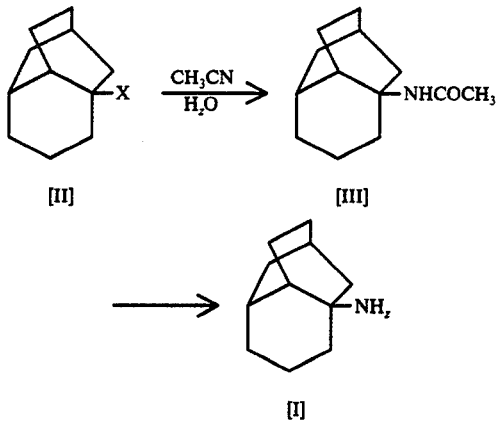

wherein X represents a chlorine, bromine or iodine atom, or an hydroxy group or acetoxy group.

DESCRIPTION OF THE PREFERRED EMBODIMENTS

In producing 3-acetylamino-4-homoisotwistane of the formula [III] from 3-substituted-4-homoisotwistane of the formula [II], sulfuric acid may be used in a concentration of more than 20%, preferably ranging from 85 to 98%. The reaction is carried at a temperature from $-20$ to $+90°$ C, particularly ranging from $+5°$ to $+50°$ C.

In producing 3-amino-4-homoisotwistane from 3-acetylamino-4-homoisotwistane of the formula [III], all generally known methods for hydrolyzing amides are applicable. That is, 3-acetylamino-4-homoisotwistane of the formula [III] may be solvalyzed in water; in water containing alkaline agents such as sodium hydroxide, potassium hydroxide, sodium carbonate, potassium carbonate and the like; in alcohols such as methanol, ethanol, propanol, ethylene glycol, diethylene glycol and the like containing the above alkaline agents; or in the mixed solvents of above alcohols and water containing the same alkaline agents.

The reaction may be conducted at a temperature ranging from $+10°$ to $+350°$ C. To accelerate hydrolysis, however, a higher temperature range is preferably used. The formed 3-amino-4-homoisotwistane of the formula [I] is so hygroscopic that its elemental analysis is made only with great difficulty.

However, the product separated from the reaction solution by gaschromatography is a white crystal and has an absorption band in the range of 3400 cm$^{-1}$ due to the stretching vibration of the N—H bond, indicating that this product possesses an amino group.

The thus obtained 3-amino-4-homoisotwistane of the formula [I] is easily reacted with various inorganic or organic acids to afford acid addition salts. Suitable acids to be used include hydrochloric acid, sulfuric acid, thiosulfuric acid, p-toluenesulfonic acid, oxalic acid, citric acid, phosphoric acid and the like. The acid addition salts are produced by methods; that is, by neutralizing 3-amino-4-homoisotwistane with an aqueous solution of the above acis and drying; or by reacting 3-amino-4-homoisotwistane with acids in nonpolar organic solvents and collecting the precipitate.

The present compound of the formula [I] and acid addition salts thereof exert extremely excellent effects on monolayer cultures of chick embryo fibroblasts cells against Newcastle disease virus, among Para-myxovirus belonging to RNA type virus, and present less cytotoxicity in their effective concentrations.

The present compounds exhibit an apparent inhibition of an viral growth in a concentration, which is only 1/10 that of adamantylamine hydrochloride which is well known as an anti-influenza virus agent.

These findings are shown by the following experimental results.

After chick embryo fibroblast cells were cultivated in a test tube for 2 to 3 days, the medium was inoculated with Newcastle disease virus of about 128 HAU (Hemagglutination Units). To the upper layer was added a culture medium of the stepwise dilution system containing the following compounds, and the resulting mixture was then cultivated at 37° C for 48 hours and the effects were evaluated based on the hemagglutination reaction.

The results obtained are shown in Table 1.

Table 1

| Compounds | Concentration (μg/ml) | % HAU* | CT** |
|---|---|---|---|
| 3-amino-4-homoiso-twistane hydrochloride | 40 | 0.4 | ± |
|  | 20 | 2.7 | − |
|  | 10 | 5.3 | − |
|  | 5 | 18 | − |
|  | 2.5 | 21 | − |
| Adamantylamine hydrochloride (Control) | 500 | <1.0 | + |
|  | 250 | 9 | + |
|  | 125 | 100 | − |
|  | 62 | 100 | − |

*% HAU = $\frac{\text{(Dilution multiple inhibiting hemagglutination)}}{\text{HAU in the blank medium}} \times 100$ HAU in the media containing the compounds

**CT: the degree of damage on chick embryo fibloblast cells exerted by the test compounds
(−) no damage
(±) small eruptions were observed on the surface of the cell.
(+) monolayer of chick embryo fibloblast cells was separated from the wall of tube.

The invention is described more specifically in terms of some Examples which are meant purely to illustrate or explain and do not impose limitations upon the invention.

EXAMPLE 1

(3-Acetylamino-4-homoisotwistane of formula III)

To a solution of 5.30g (0.022 mole) of 3-bromo-4-homoisotwistane in 40 ml of acetonitrile was added dropwise 100 ml of 95% sulfuric acid with stirring over a period of 30 minutes at room temperature. After the dropwise addition, the mixture was further stirred at room temperature for 20 hours. After the completion of the reaction, the reaction mixture was poured into 200 ml of ice-water and the resulting solution was extracted twice with 100 ml of diethylether. The extract was washed with 100 ml of water and dried over anhydrous sodium sulfate. The ether layer was filtered and the filtrate was concentrated. Recrystallization from diethylether afforded 3.8g (yield 83%) of white crystals having a melting point of 125°–126° C (in a sealed tube).

Elemental Analysis: as $C_{18}H_{21}NO$
Calculated (%): C: 75.3 H: 10.2 N: 6.7
Found (%): C: 75.1 H: 9.9 N: 6.6
ir (nujol, cm$^{-1}$)
3300 (γ N—H), 1640 (γ C=O), 1540 (δ N—H), 1310, 740
pmr (solvent: CCl$_4$; internal standard: TMS, δ)
2.1–1.2 (complex multiplet)
2.2 (singlet,

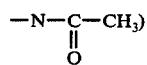
—N—C—CH$_3$)
 ‖
 O ms m/e (relative strength)
207(M$^+$; 42), 148(100), 136(25), 119(21), 94(41), 91(17),
79(19), 60(36), 43(19), 18(19)

EXAMPLE 2

The same procedure of Example 1 was repeated under the same reaction condition, with the exception that 3-substituted (X=Cl, I, OH, OCOCH$_3$ in the formula II) 4-homoisotwistane was used instead of 3-bromo-4-homoisotwistane, and there was obtained the same product. Its yield before recrystallization was in the vicinity of that in Example 1.

EXAMPLE 3

(3-Amino-4-homoisotwistane [I] and its acid salts)

An amount of 8.4g (0.21 mole) of sodium hydroxide was dissolved in 60ml of diethylene glycol by application of heat, and to the solution was added 5.22g (0.025 mole) of 3-acetylamino-4-homoisotwistane. The resulting mixture was stirred under reflux conditions for 5 hours. After cooling, the mixture was poured into 200ml of water and extracted three times with 50ml of diethylether. The extract was dried over anhydrous potassium carbonate to evaporate the solvent, and 2.63 g (yield 64%) of crude 3-amino-4-homoisotwistane were obtained. This product was so hygroscopic that it deliquesced immediately. This was dissolved in 50 ml of diethylether and the resulting solution was dried over anhydrous potassium carbonate. An anhydrous hydrogen chloride gas was bubbled into the mixture, and evaporation of the solvent gave rise to 3.1 g of 3-amino-4-homoisotwistane hydrochloride as colourless crystals.

Elemental Analysis: as $C_{11}H_{20}NCl$
Calculated (%): C: 65.5 H: 9.9 N: 7.0 Cl: 17.6
Found (%): C: 65.2 H: 9.7 N: 7.0 Cl: 18.0
ir (nujol, cm$^{-1}$)
3200 – 2900 (broad, N$^{+-}$H stretching vibration)
2020, 1610 (N$^{+-}$H deformation vibration)
1510 (N$^{+-}$H deformation vibration)
ms (m/e, relative strength)
Parent peak was not recognized, but a peak of 3-amino-4-homoisotwistane was observed.
165(10), 96(10), 57(11), 56(100), 44(13), 43(14), 41(14),
30(16), 28(14), 18(82), 17(20)

EXAMPLE 4

In a pressure-proof container were placed 1.65g (0.01 mole) of 3-acetylamino-4-homoisotwistane and 50ml of water and the mixture was stirred at 250° C for 20 hours. After cooling, the reaction mixture was extracted twice with 30ml of ether. The ether layer was extracted with 50ml of 1.2N hydrochloric acid solution and the aqueous layer was adjusted to pH12 with conc. sodium hydroxide solution, then extracted twice with 30ml of ether. The extract was dried over anhydrous potassium carbonate and filtered to separate potassium carbonate.

An anhydrous hydrogen chloride gas was bubbled into the ether solution to remove the solvent, and there was obtained 1.44g (yield 72%) of 3-amino-4-homoisotwistane hydrochloride.

What we claim is:
1. 3-Aminotricyclo [5.3.1.0$^{3,8}$] undecane and acid addition salts thereof.
2. A process for producing 3-aminotricyclo [5.3.1.0$^{3,8}$] undecane which comprises reacting acetonitrile with a compound of the formula:

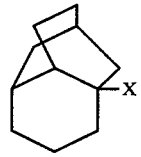

wherein X is Cl, Br, I, OH or COCH$_3$, in the presence of H$_2$SO$_4$ and hydrolyzing the resultant 3-acetylaminotricyclo [5.3.1.0$^{3,8}$] undecane.
3. The process of claim 2, wherein the hydrolysis is conducted in alcohol in the presence of an alkaline agent.
4. The process of claim 2, wherein the hydrolysis is conducted in water by application of heat.

* * * * *